United States Patent [19]

Coston et al.

[11] Patent Number: 4,490,053
[45] Date of Patent: Dec. 25, 1984

[54] TEMPERATURE THRESHOLD DETECTOR

[75] Inventors: Charles J. Coston, Sunnyvale; Euel V. Higgins, San Jose, both of Calif.

[73] Assignee: Lockheed Missiles & Space Company, Inc., Sunnyvale, Calif.

[21] Appl. No.: 485,241

[22] Filed: Apr. 15, 1983

[51] Int. Cl.³ .................. G01N 25/72; F16L 55/04
[52] U.S. Cl. .................................. 374/5; 374/163;
374/179; 338/26; 338/214; 340/596
[58] Field of Search ............... 338/26, 214, 22 R;
340/596; 219/504, 505; 337/14; 374/185, 4,
186, 10, 179, 163; 346/33 TP; 136/230

[56] References Cited

U.S. PATENT DOCUMENTS

| 2,413,125 | 12/1946 | Walbridge | 338/26 |
| 2,495,867 | 1/1950 | Peters | 338/26 X |
| 2,659,067 | 11/1953 | Peters | 340/596 |
| 2,740,874 | 4/1956 | Kelly et al. | 338/26 |
| 2,764,659 | 9/1956 | Postal | 340/596 |
| 2,796,455 | 6/1957 | Jones | 338/26 X |
| 2,805,272 | 9/1957 | Postal | 340/596 X |
| 2,842,648 | 7/1958 | Reynolds | 338/26 |
| 2,848,587 | 8/1958 | Postal | 338/26 |
| 2,936,434 | 5/1960 | Postal | 338/26 |
| 2,941,192 | 6/1960 | Postal | 340/596 X |
| 3,408,607 | 10/1968 | Davis | 338/26 |
| 3,416,971 | 12/1968 | Hutkin | 338/26 X |
| 3,577,193 | 5/1971 | Irving | 340/596 X |
| 3,683,696 | 8/1972 | Vaughan et al. | 338/26 X |
| 3,911,727 | 10/1975 | Katsuta et al. | 374/4 |

FOREIGN PATENT DOCUMENTS

| 662529 | 5/1963 | Canada | 338/26 |
| 754767 | 3/1967 | Canada | 338/26 |
| 1013800 | 12/1965 | United Kingdom | 340/596 |

OTHER PUBLICATIONS

Porral and Mattendi, "A Device for Determining the Position of a hot Spot & it's Temperature Between 1000°–1700° C.", High Pressure High Temperatures, 1972, vol. 4, #2 pp. 225-228.

Primary Examiner—C. L. Albritton
Assistant Examiner—C. N. Sears
Attorney, Agent, or Firm—John J. Morrissey

[57] ABSTRACT

A temperature threshold detector (10) comprises a first electrical conductor (11) and a second electrical conductor (12), which are separated by a spacing structure (13). The first and second electrical conductors (11 and 12) are made of metals that are dissimilar from each other in terms of oxidation potentials or thermally generated electromotive force. The spacing structure (13) is made of a material whose electrical resistivity is temperature dependent so that, when exposed to a temperature below a predetermined threshold value, the spacing structure (13) provides electrical isolation between the first and second electrical conductors (11 and 12). However, when exposed to a temperature above the predetermined threshold value, the spacing structure (13) enables an electromotive force to develop across the first and second conductors (11 and 12). This electromotive force is indicative of temperature rise above the predetermined threshold.

20 Claims, 8 Drawing Figures

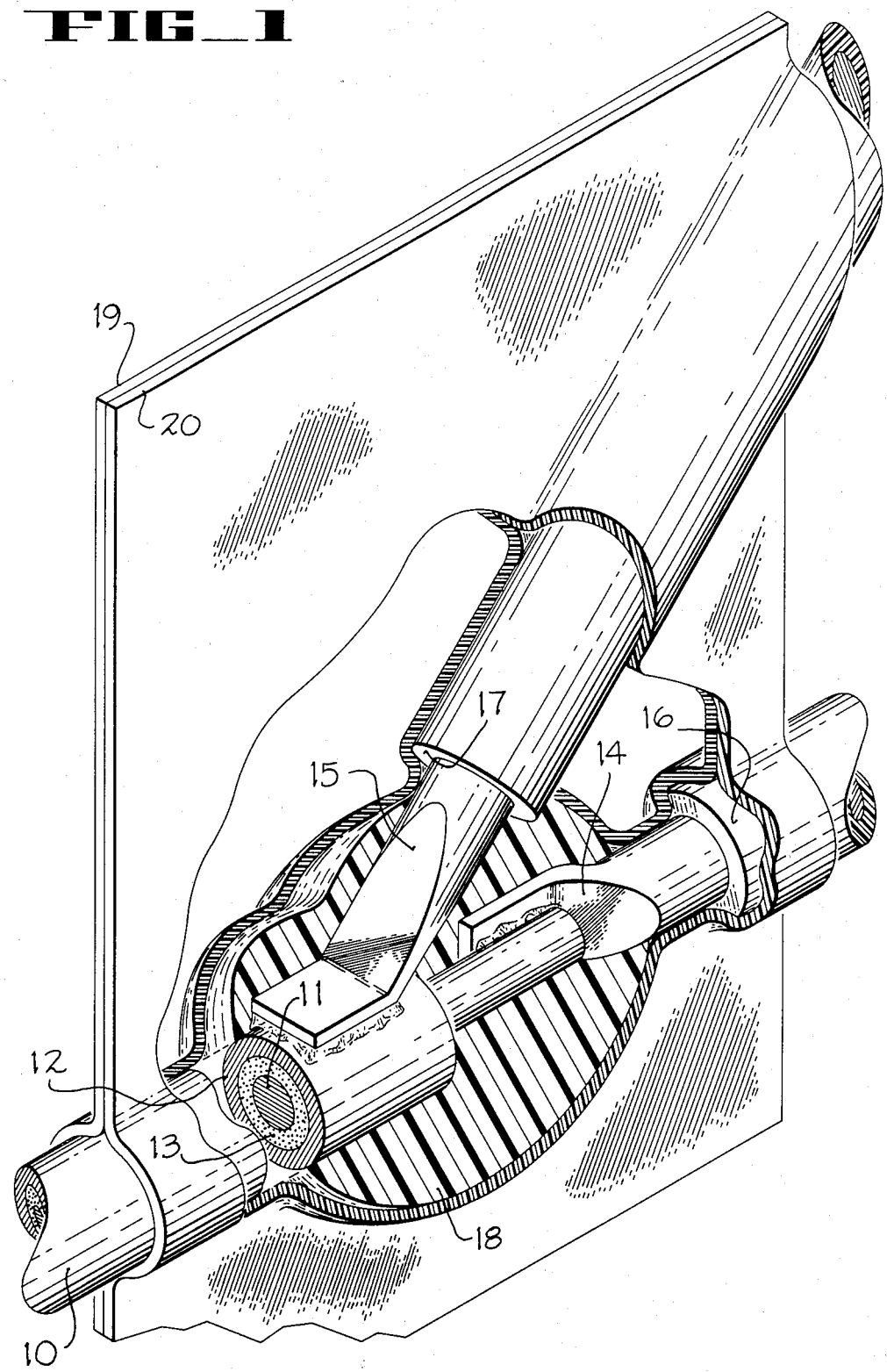
FIG_1

FIG_2
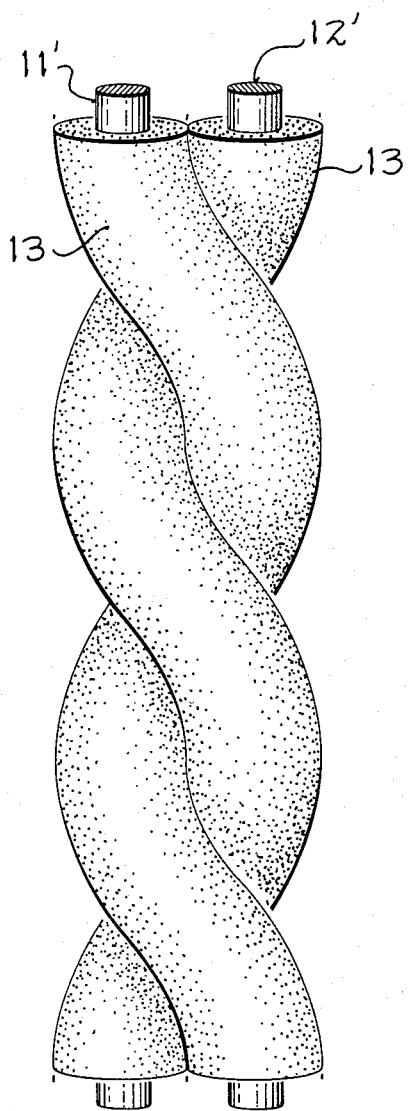
FIG_3
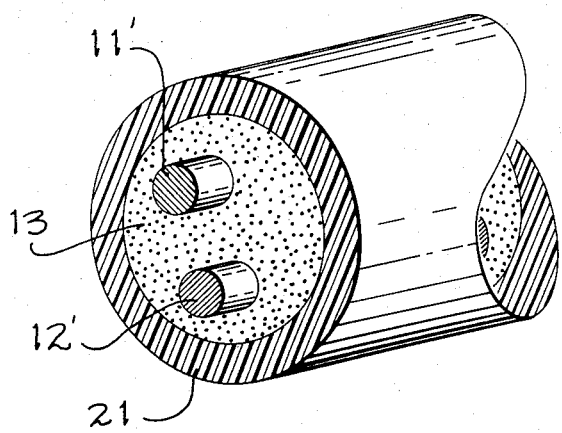
FIG_4
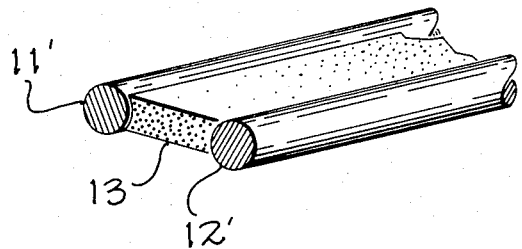

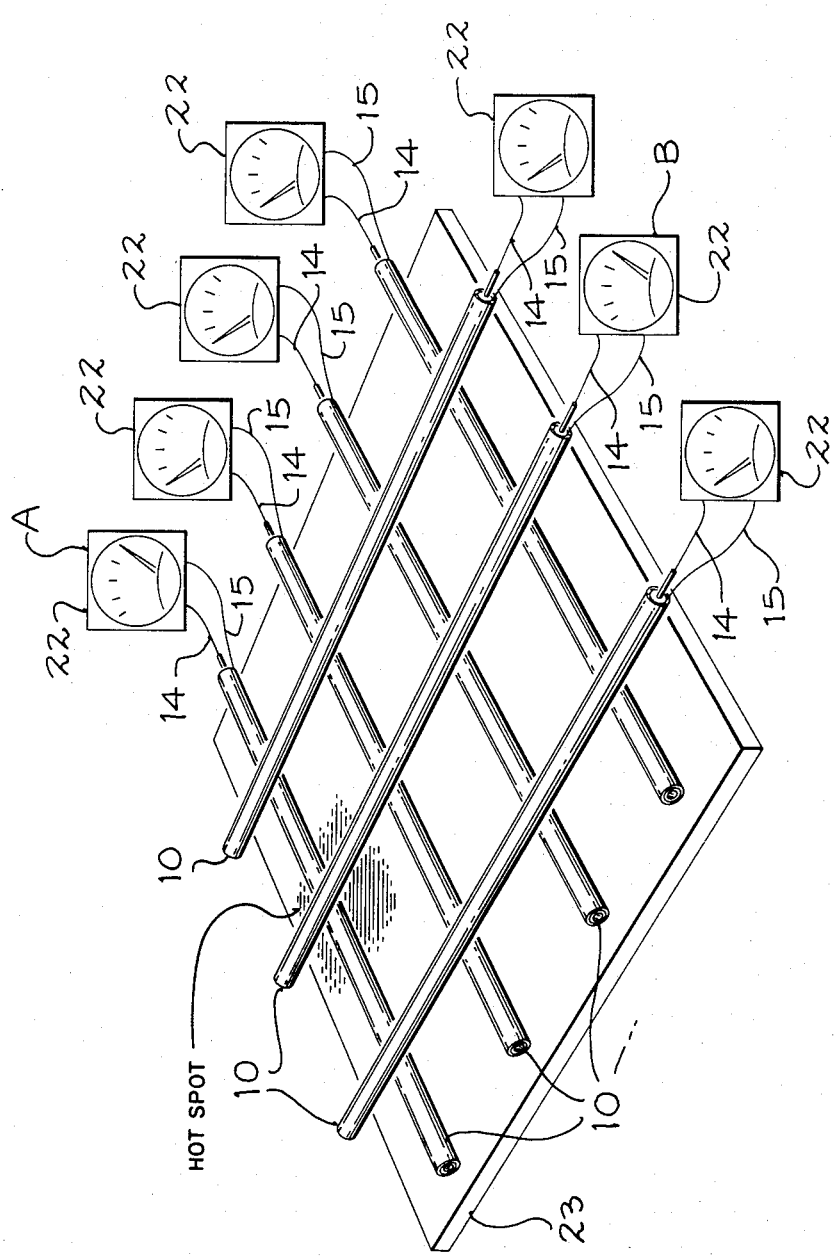
FIG_5

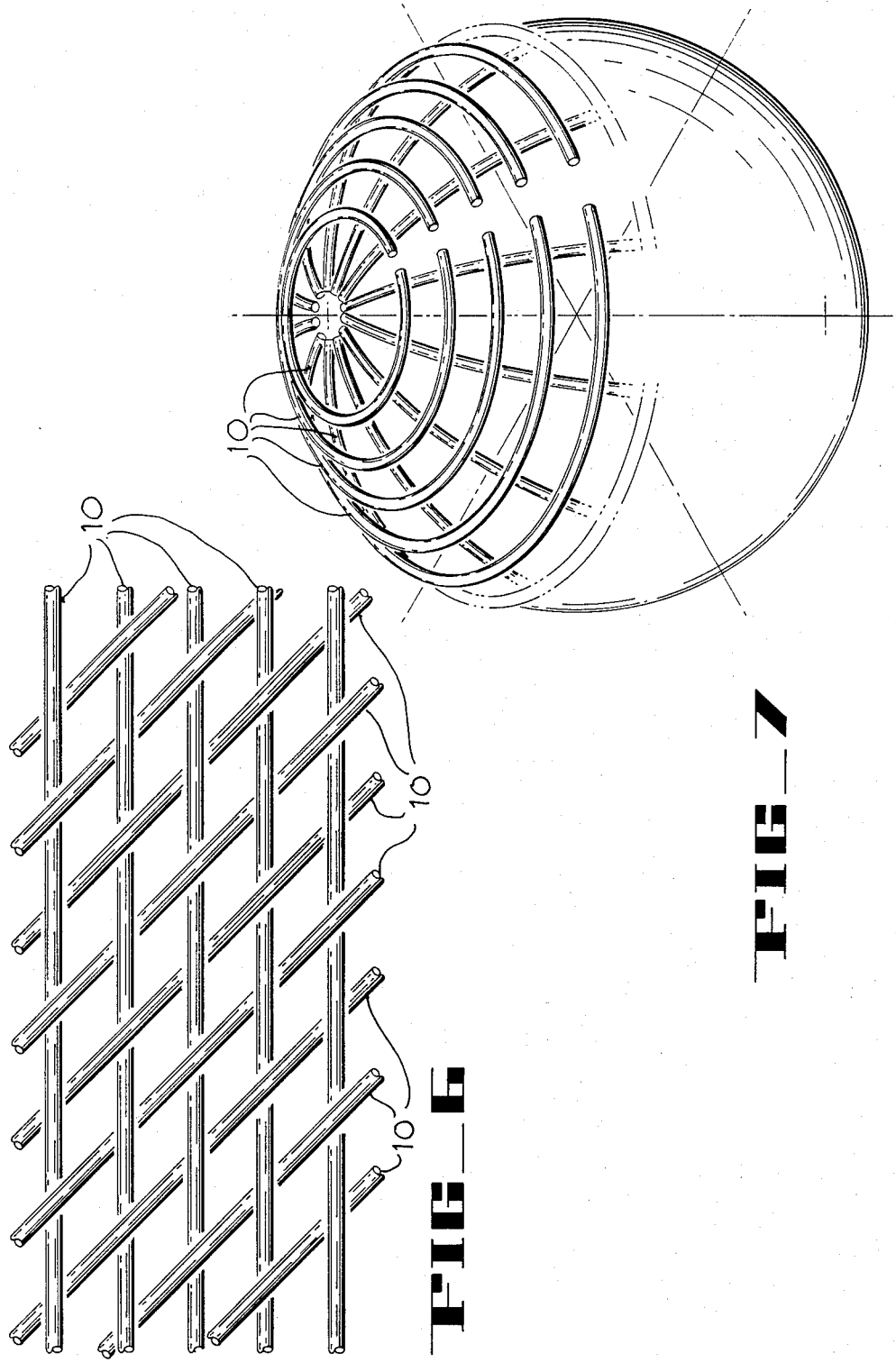

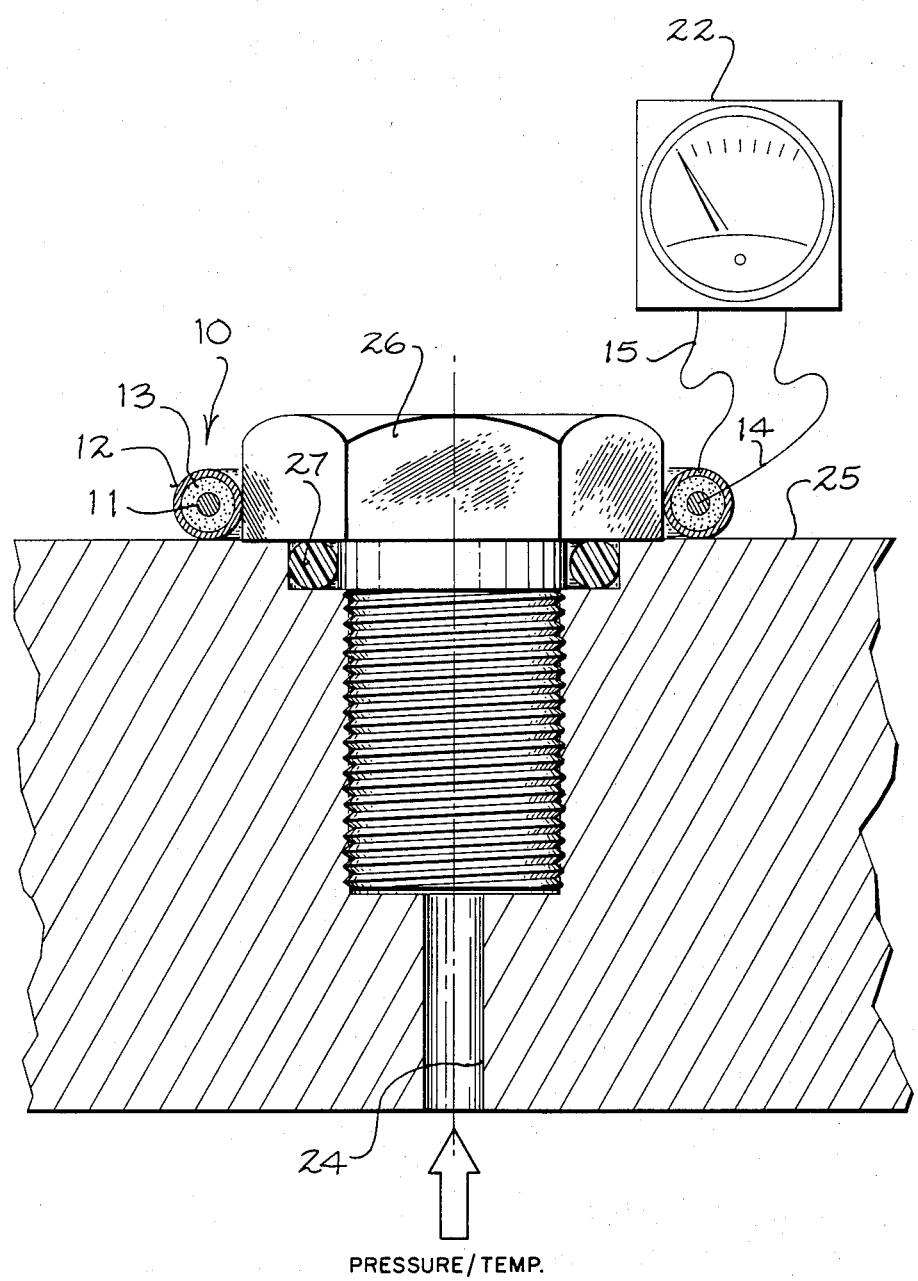
FIG_8
PRESSURE/TEMP.

TEMPERATURE THRESHOLD DETECTOR

TECHNICAL FIELD

This invention relates to thermal survey instrumentation, and particularly to temperature threshold detectors for use in thermal survey instrumentation.

The Government has rights in this invention pursuant to Contract N00030-81-C-0081 awarded by the Department of the Navy.

DESCRIPTION OF THE PRIOR ART

Thermal survey instrumentation is used in verifying design adequacy, locating failure precursors, and analyzing failures of internal components and materials in apparatus such as, e.g., ballistic missile flight motor. Conventionally, a thermal survey to monitor the performance of a large structure involves positioning a number of thermocouple devices in thermal contact with the structure in a pattern that enables any thermal manifestation of design inadequacy or incipient failure (i.e., any "hot spot") occurring in the structure to be detected. The pattern in which the thermocouple devices must be arranged in order to provide an adequate thermal survey is determined by the configuration of the structure.

In the case of a ballistic missile flight motor, the motor casing would typically have a cylindrical diameter of approximately two meters and a length of approximately six meters. To provide an in-flight thermal survey of the functioning of the motor using conventional thermal survey instrumentation, an array of approximately 3600 thermocouple devices would be positioned in thermal contact with the motor casing in a pattern that would enable the occurrence of a "hot spot" within three inches of any one of the thermocouple devices to be detected. A telemetry system capable of receiving and processing temperature signals from each one of the thermocouple devices would also be necessary. Thus, electrical leads to approximately 3600 separate thermocouple devices would be necessary, and electronic components and circuitry for processing signals from each of these 3600 thermocouple devices would be required.

A need was perceived in the prior art for thermal survey instrumentation capable of detecting "hot spot" that might occur randomly within a very large structure, without requiring a practically unmanageable number of electrical leads, and without requiring an extraordinarily large signal processing capability.

SUMMARY OF THE INVENTION

It is an object of the present invention to provide instrumentation for detecting thermal manifestations of design inadequacy and/or incipient failure in large structures such as a ballistic missile flight motors.

It is a particular object of the present invention to provide thermal survey instrumentation for detecting thermal manifestations of design inadequacy and/or incipient failure in large structures, where operational requirements restrict the number of electrical leads that can be used and limit the signal processing capability that can be made available.

A temperature threshold detector according to the present invention comprises two electrical conductors made of dissimilar metals, which are separated by a spacing structure made of a material whose electrical resistivity varies with temperature change from one side to the other of a relatively narrow threshold range of temperature. The metals of which the electrical conductors are made are dissimilar in terms of their oxidation potentials or thermally generated electromotive force. The material of which the spacing structure is made provides electrical isolation between the two conductors when the temperature is on one side of the threshold range, and enables a self-generated electromotive force to occur across the two conductors when the temperature is on the other side of the threshold range.

Criteria for selection of the spacing structure material were discussed in a paper entitled "A New Temperature Threshold Detector—Application to Missile Monitoring" by C. J. Coston and E. V. Higgins, which was published in the Proceedings of the 28th International Instrumentation Symposium, in May 1982, pages 701–705.

When the temperature threshold detector is used to detect "hot spots", it is expedient that the spacing structure material function as an electrical insulator below a well-defined narrow temperature threshold range, and that the spacing structure material enable an electromotive force to occur across the conductors when the temperature rises above the threshold range. Furthermore, the difference between the electrical resistivity values of the spacing structure material above and below the temperature threshold range should be readily discernible. Ideally, the spacing structure material would have infinite direct current resistivity below a designated temperature threshold value, and zero direct current resistivity above that designated temperature threshold value, with an abrupt transition from infinite resistivity to zero resistivity at the designated temperature threshold value. As a practical matter, the difference in electrical resistivity of the spacing structure material from one side to the other of the temperature threshold range should be at least one order of magnitude. For most applications, the temperature threshold range would be less than about 50 degrees C.

It would ordinarily be required that the spacing structure material be chemically stable in air, nonhygroscopic, nontoxic and relatively inexpensive. In light of these requirements, certain ionic solids and semiconductor materials have been found to be especially suitable for the spacing structure material. Among ionic solids, potassium nitrate ($KNO_3$) and sodium nitrate ($NaNO_3$) are suitable. Among semiconductor materials, transition metal oxides such as manganese oxide ($MnO$), nickel oxide ($NiO$), ferrous oxide ($FeO$) and cobaltous oxide ($CoO$) are suitable.

The particular material used in fabricating the spacing structure is selected on the basis of requirements imposed by the particular application. Thus, the temperature range to which the temperature threshold detector would be exposed, and the issue of whether the spacing structure material would be chemically stable in the temperature range of interest, are of paramount importance in selecting the spacing structure material. In specific applications, corrosive characteristics and/or toxicity would be significant considerations in selecting the spacing structure material.

If the spacing structure is made of an ionic solid, the primary component of the self-generated electromotive force that occurs across the dissimilar metal conductors when the temperature rises above the temperature threshold range is attributable to an increase in ionic mobility, which results in galvanic activity between the conductors. Another component of the total electromotive force occurring across the conductors when the spacing structure is an ionic solid is attributable to a quasithermocouple effect, which is due to the fact that a thermocouple-like junction is formed between the dissimilar metal conductors. The component of electromotive force attributable to this quasithermocouple effect may add to or subtract from the component of electromotive force attributable to galvanic activity. However, the magnitude of the component of electromotive force attributable to galvanic activity exceeds the magnitude of the component of electromotive force attributable to the quasithermocouple effect by, typically, more than an order of magnitude. Consequently, when the spacing structure is made of an ionic solid, the electromotive force attributable to galvanic activity is the predominant component of the total electromotive force.

If the spacing structure is made of a semiconductor material, the self-generated electromotive force occurring across the conductors when the temperature rises above the temperature threshold range is attributable to the quasithermocouple effect.

A temperature threshold detector according to the present invention is elongate. A number of such individual temperature threshold detectors can be arranged in thermal contact with a structure to form a thermal survey grid for detecting hot spots in the structure. Each temperature threshold detector of the grid can independently sense a hot spot in the structure anywhere along the length of the detector. The grid can be configured to assume the general contours of the structure.

Using a number of temperature threshold detectors according to the present invention to form a thermal survey grid requires electrical leads to each of the temperature threshold detectors. However, the total number of temperature threshold detectors comprising the grid is much less than the number of individual thermocouple devices that would otherwise be necessary to provide an equivalent thermal survey capability using instrumentation techniques of the prior art.

A system for managing a thermal survey using a grid of temperature threshold detectors in accordance with the present invention must be capable of processing signals from each of the temperature threshold detectors comprising the grid. However, the signal processing capability of such a system is much lower than would be required in the prior art, because fewer measurements are needed using a grid of temperature threshold detectors according to the present invention.

DESCRIPTION OF THE DRAWING

FIG. 1 is a perspective view, partly in cross section, in which an end portion of an elongate temperature threshold detector according to the present invention is shown attached to electrical leads of a volt-meter.

FIG. 2 is a perspective cross-sectional view indicating an alternative configuration for the temperature threshold detector of FIG. 1.

FIG. 3 is a perspective cross-sectional view indicating another alternative configuration for the temperature threshold detector of FIG. 1.

FIG. 4 is a perspective cross-sectional view indicating yet another alternative configuration for the temperature threshold detector of FIG. 1.

FIG. 5 is a perspective view illustrating a thermal survey grid comprising a number of elongate temperature threshold detectors of the type shown in FIG. 1.

FIG. 6 is a perspective view illustrating an interwoven arrangement for the temperature threshold detectors of the thermal survey grid of FIG. 5.

FIG. 7 is a perspective view illustrating a nonplanar arrangement for the temperature threshold detectors of the thermal survey grid of FIG. 5.

FIG. 8 is a cross-sectional view indicating a sealed closure in a containment-vessel wall, and illustrating placement of a temperature threshold detector according to the present invention adjacent the sealed closure to detect the occurrence of a leak.

BEST MODE OF CARRYING OUT THE INVENTION

An end portion of an elongate temperature threshold detector 10 according to the present invention is shown in cross-sectional detail in FIG. 1. The temperature threshold detector 10 comprises a central wire 11 made of a first metal, an outer sheath 12 made of a second metal, where the first and second metals are dissimilar in terms of oxidation potentials or thermally generated electromotive force, and an annular spacing structure 13 separating the central wire 11 from the outer sheath 12. The central wire 11, the spacing structure 13, and the outer sheath 12 are disposed coaxially with respect to each other.

The central wire 11 and the outer sheath 12 could in principle be made from any of the so-called transition elements, including the rare earth elements, intervening between Group II and Group III of the Periodic Table of Elements. Alternatively, the central wire 11, or the outer sheath 12, or both, could be made from alloys of any of the transition elements. The fundamental requirement is that the central wire 11 be made from a metal that is dissimilar to the metal from which the outer sheath 12 is made in terms of oxidation potentials or thermally generated electromotive force. It has been convenient in practice to fabricate the central wire 11 from commercial grade copper, and to fabricate the outer sheath 12 from a commercial grade Monel alloy.

The function of the spacing structure 13 is to serve as an electrical insulator between the central wire 11 and the outer sheath 12 when the temperature all along the temperature threshold detector 10 is below a predetermined narrow transition range, and to provide a self-generated electromotive force between the central wire 11 and the outer sheath 12 when the temperature of any portion of the temperature threshold detector 10 reaches or exceeds the predetermined transition range. For most applications, the spacing structure 13 would made of a material that is chemically stable in air and not hygroscopic. Furthermore, the spacing structure material would preferably be nontoxic and relatively inexpensive.

If the spacing structure 13 is made of an ionic solid, galvanic activity occurs between the dissimilar metals comprising the central wire 11 and the outer sheath 12, respectively, when the temperature reaches the transition temperature range. In addition, a thermocouple-like effect occurs between the two dissimilar metals. The galvanic effect and the thermocouple-like effect result in a net electromotive force between the central wire 11 and the outer sheath 12. If the spacing structure is made of a semiconductor material, only the thermocouple-like effect occurs between the two dissimilar metals. In either case, a voltmeter connected across the central wire 11 and the outer sheath 12 can detect this self-generated electromotive force, which indicates that the temperature of some portion of the temperature threshold detector 10 has risen above a predetermined value.

In considering available materials as candidates from which to make the spacing structure 13, compromises must be made with regard to the temperature-related electrical characteristics of the various candidate materials. As discussed in "A New Temperature Threshold Detector—Application to Missile Monitoring", op. cit., potassium nitrate ($KNO_3$) was determined to be a suitable ionic solid from which to make the spacing structure 13. Potassium nitrate undergoes a change in electrical resistivity from a value of about $10^8$ ohm-cm to a value of about $10^5$ ohm-cm in passing through the relatively narrow-transition temperature range from about 300 degrees C. to about 350 degrees C. In addition, potassium nitrate is chemically stable in air and is non-hygroscopic and nontoxic.

A semiconductor material that has been determined to be a suitable material from which to manufacture the spacing structure 13 is a mixture of 80% manganese oxide (MnO) and 20% nickel oxide (NiO), which undergoes a change in electrical resistivity from about $10^5$ ohm-cm to about $10^3$ ohm-cm in passing through a transition temperature range from about 200 degrees C. to about 300 degrees C. It has been found that a 10% dilution of the semiconductor mixture with alumina ($Al_2O_3$) increases response linearity.

The temperature threshold detector 10 can be fabricated by conventional wire drawing techniques. Prototype temperature threshold detectors of the configuration shown in FIG. 1 have been fabricated for Lockheed Missiles & Space Company, Inc. by California Fine Wire Corporation, Grover City, Calif.

In operation, the temperature threshold detector 10 is placed in thermal contact with a structure that is to be monitored for the occurrence of a "hot spot" (i.e., a thermal manifestation of some undesired event). The electrical circuit between the central wire 11 and the outer sheath 12 remains "open" as long as all portions of the spacing structure 13 remain at a temperature below the temperature threshold range determined by the nature of the material comprising the spacing structure 13. However, whenever the temperature of any portion of the temperature threshold detector 10 rises to a value within or exceeding the temperature threshold range for the particular spacing structure material, the temperature threshold detector 10 provides an electromotive force in response to the temperature rise.

In FIG. 1, the end of the temperature threshold detector 10 remote from the structure being monitored is shown connected to electrical leads 14 and 15. The leads 14 and 15 electrically connect the temperature threshold detector 10 to a conventional voltmeter or other device for indicating the presence of an electromotive force between the central wire 11 and the outer sheath 12. The central wire 11, which extends coaxially beyond the spacing structure 13 and outer sheath 12, is shown electrically connected by a soldered joint to a flattened end portion of the electrical lead 14. Similarly, the outer sheath 12 is shown connected by a soldered joint to a flattened end portion of the electrical lead 15. The electrical leads 14 and 15, except for their end portions as shown in FIG. 1, are surrounded by insulating sleeves 16 and 17, respectively.

The end of the temperature threshold detector 10, and the flattened ends of the electrical leads 14 and 15 connected thereto, are encased in a potting material such as Emerson Cummings Stycast 2762FT to form an encapsulation 18, which provides mechanical rigidity and support for the soldered electrical joints. The encapsulation 18 and the adjacent ends of the detector 10 and of the electrical leads 14 and 15 can be sandwiched between two layers 19 and 20 of Kapton tape, which serves to protect the encapsulation 18 from abrasion and/or fracturing.

The internal configuration of the temperature threshold detector 10 is not critical to the invention. For particular applications, configurations other than the coaxial configuration shown in FIG. 1 might be preferable. Alternative configurations for the temperature threshold detector 10 are shown in FIGS. 2, 3 and 4.

In the configuration of FIG. 2, the electrical conductors comprising the temperature threshold detector 10 are disposed as a twisted pair of wires 11' and 12', each of which is coated with the material comprising the spacing structure 13. In the configuration of FIG. 3, the electrical conductors are disposed as a pair of parallel wires 11' and 12', which are encased in the material comprising the spacing structure 13. The spacing structure 13 is of generally cylindrical configuration, and is shown surrounded by an electrically insulating protective sleeve 21. In particular applications, however, a metallic protective sleeve might be appropriate. In FIG. 4, the electrical conductors are disposed as a pair of generally parallel wires 11' and 12', which are maintained in side-by-side disposition by the spacing structure 13. The spacing structure 13 has a generally flat configuration with opposite side portions that are contoured to receive the cylindrically configured wires 11' and 12'.

As indicated schematically in FIG. 5, a number of elongate temperature threshold detectors 10 in accordance with the present invention, each of which is connected to a particular one of a corresponding number of voltmeters 22, can be arranged in a gridded pattern to enable a thermal survey to be made of an extended structure 23. The occurrence of a "hot spot" at any location on the structure 23, as indicated by the legend in FIG. 5, would cause a voltage to be detected in each of two temperature threshold detectors 10 in thermal contact with the "hot spot". In FIG. 5, the temperature threshold detectors 10 that sense the "hot spot" are shown connected to the voltmeters labelled A and B. The occurrence of non-zero voltage readings on the voltmeters A and B indicates the coordinates of the "hot spot" on the gridded thermal survey pattern.

The temperature threshold detectors 10 could be either rigid or flexible. In FIG. 6, a fragmentary view is provided of an interwoven arrangement of temperature threshold detectors 10 forming a blanket-like thermal survey covering for the structure that is to be monitored for the occurrence of "hot spots". The gridded pattern in which the temperature threshold detectors 10 are arranged could be contoured to conform to the configuration of the structure being monitored. In FIG. 7, a hemispherically contoured gridded pattern of temperature threshold detectors 10 is shown by way of example.

A particular application for a temperature threshold detector in accordance with the present invention is illustrated in FIG. 8, in which the temperature threshold detector 10 is positioned circumjacent a sealed port 24 in a wall 25 of a vessel for confining a high-pressure, high-temperature gas. The wall 25 could be, for example, the igniter adapter of a rocket motor casing. The port 24 is closed by a threaded plug 26, which is configured as a conventional threaded bolt. The outer surface of the wall 25 circumjacent the port 24 is recessed to receive a compressible O-ring 27, which is positioned around the shank and under the head of the plug 26. As the plug 26 is screw-threaded into the port 24, the head of the plug 26 compresses the O-ring 27 to form a gas-tight seal between the plug 26 and the wall 25. If a leak were to develop in the O-ring 27 so as to allow high-temperature gas to exit from the pressure vessel through the port 24, the leaking high-temperature gas would heat the temperature threshold detector 10 and thereby cause an electromotive force to be generated between the two electrical conductors 11 and 12. This electromotive force would be sensed by the volt-meter 22, which would thereby indicate the occurrence of the leak.

Particular embodiments of a temperature threshold detector in accordance with the present invention have been described herein. Also, particular embodiments of a thermal survey grid comprising a number of temperature threshold detectors have been described. However, other embodiments of a temperature threshold detector in accordance with the present invention, and of thermal survey apparatus using such a temperature threshold detector in accordance with the present invention, which would be more suitable for particular applications, would be apparent to workers skilled in the art upon perusal of the foregoing specification and accompanying drawing. Thus, the descriptions presented herein are to be understood as being illustrative of the invention, which is more generally defined by the following claims and their equivalents.

We claim:
1. An apparatus for detecting a rise in temperature that exceeds a predetermined threshold value, said apparatus comprising:
   (a) a sensor positionable in proximity to a device that is to be monitored for temperature change, and
   (b) an instrument for indicating temperature rise exceeding said threshold value said instrument being driven by an electromotive force that is self-generated by said sensor when the temperature in said device rises above said threshold value,
where said sensor includes:
   (i) a first electrical conductor,
   (ii) a second electrical conductor, and
   (iii) a spacing structure separating said first and second electrical conductors,
said first and second electrical conductors being made of dissimilar metals, said spacing structure being made of an ionic salt selected from the group consisting of $KNO_3$ and $NaNO_3$, said ionic salt having an electrical resistivity that is temperature dependent so that said spacing structure when exposed to temperatures below said threshold value provides substantial electrical isolation between said first and second electrical conductors, and so that said spacing structure when exposed to temperatures above said threshold value acts with the dissimilar metals of said first and second electrical conductors to cause said self-generated electromotive force to develop across said first and second electrical conductors, and
where said instrument for indicating temperature rise includes a first electrical lead connected to said first electrical conductor and a second electrical lead connected to said second electrical conductor, said electromotive force developed across said first and second electrical conductors thereby driving said instrument to indicate temperature rise exceeding said threshold value.

2. The apparatus of claim 1 wherein said first and second electrical conductors are elongate, said spacing structure being correspondingly elongate, whereby a rise in temperature exceeding said threshold value at any position along said sensor can be indicated.

3. The apparatus of claim 2 wherein said first electrical conductor is configured as a wire, and said second electrical conductor is configured as a sheath disposed around but spaced from said wire.

4. The apparatus of claim 3 wherein said second electrical conductor is configured as a generally cylindrical sheath disposed coaxially around said wire, said spacing structure being of generally annular configuration separating said sheath from said wire.

5. The apparatus of claim 2 wherein said first and second electrical conductors are configured as wires.

6. The apparatus of claim 5 wherein said spacing structure is of generally flat configuration with edges configured to receive said wires.

7. The apparatus of claim 5 wherein said spacing structure is disposed around said first wire, said second wire being in contact with said spacing structure.

8. The apparatus of claim 7 wherein said first and second electrical conductors are embedded in said spacing structure.

9. The apparatus of claim 8 further comprising a protective sleeve disposed around said spacing structure.

10. The apparatus of claim 7 wherein said spacing structure comprises a first portion disposed around said first electrical conductor and a second portion disposed around said second electrical conductor, said first electrical conductor and surrounding first portion of said spacing structure being positioned adjacent and in twisted relationship with respect to said second electrical conductor and surrounding second portion of said spacing structure.

11. The apparatus of claim 1 wherein said first and second electrical conductors are made of dissimilar metals selected from the group consisting of transition elements.

12. The apparatus of claim 11 wherein said first and second electrical conductors are made of dissimilar metals selected from the group of transition elements consisting of rare earth elements.

13. The apparatus of claim 1 wherein one of said first and second electrical conductors is made of an alloy, a constituent of said alloy being selected from the group consisting of transition elements.

14. The apparatus of claim 1 wherein one of said first and second electrical conductors is made of copper.

15. The apparatus of claim 14 wherein said first electrical conductor is made of copper, and wherein said second electical conductor is made of an alloy of copper and nickel.

16. A thermal survey apparatus for indicating location of a temperature rise above a predetermined value in a device to be monitored for temperature change, said thermal survey apparatus comprising a plurality of elongate temperature threshold detectors, each of said temperature threshold detectors being capable of independently indicating temperature rise above said predetermined value, said temperature threshold detectors being positionable in thermal contact with said device so that an occurrence of temperature rise above said predetemined value in said device can be independently indicated by at least two of said temperature threshold detectors in order to provide coordinates for locating said temperature rise above said predetermined value in said device, each of said temperature threshold detectors including:

(a) a sensor positionable in thermal contact with said device, said sensor having:
  (i) a first electrical conductor,
  (ii) a second electrical conductor, and
  (iii) a spacing structure separating said first and second electrical conductors,
  said first and second electrical conductors being made of dissimilar metals, said spacing structure being made of an ionic salt selected from the group consisting of $KNO_3$ and $NaNO_3$, said ionic salt having an electrical resistivity that is temperature dependent so that said spacing structure when exposed to temperatures below said predetermined value provides substantial electrical isolation between said first and second electrical conductors, and so that said spacing structure when exposed to temperatures above said predetermined value acts with the dissimilar metals of said first and second electrical conductors to cause a self-generated electromotive force to develop across said first and second electrical conductors, and (b) an instrument for indicating temperature rise above said predetermined value, said instrument having a first electrical lead connected to said first electrical conductor and a second electrical lead connected to said second electrical conductor, said electromotive force driving said instrument.

17. The thermal survey apparatus of claim 16 wherein said temperature threshold detectors are arranged in a generally planar grid.

18. The thermal survey apparatus of claim 17 wherein said temperature threshold detectors are interwoven with respect to each other.

19. The thermal survey apparatus of claim 16 wherein said temperature threshold detectors are arranged in a contoured grid pattern conforming generally to contours of said device to be monitored for temperature change.

20. An apparatus for detecting a leak in a vessel seal, said apparatus comprising:

(a) an elongate sensor responsive to a temperature rise above a predetermined value, said temperature rise being attributable to the leak in said seal, said sensor being positionable circumjacent said seal, said sensor comprising:
  (i) a first electrical conductor,
  (ii) a second electrical conductor, and
  (iii) a spacing structure separating said first and second electrical conductors,
  said first and second electrical conductors being made of dissimilar metals, said spacing structure being made of an ionic salt selected from the group consisting of $KNO_3$ and $NaNO_3$, said ionic salt having an electrical resistivity that is temperature dependent so that said spacing structure provides substantial electrical isolation between said first and second electrical conductors when exposed to a temperature below said predetermined value, and so that said spacing structure acts with the dissimilar metals of said first and second electrical conductors when exposed to a temperature above said predetermined value to cause a self-generated electromotive force to develop across said first and second electrical conductors, and (b) an instrument for indicating temperature rise above said predetermined value, said instrument having a first electrical lead connected to said first electrical conductor and a second electrical lead connected to said second electrical conductor, said electromotive force driving said instrument to indicate said leak.

* * * * *